US009168194B2

(12) United States Patent
Vyasarao

(10) Patent No.: US 9,168,194 B2
(45) Date of Patent: Oct. 27, 2015

(54) INCUBATOR AND METHOD THEREOF

(71) Applicant: General Electric Company, Schenectady, NY (US)

(72) Inventor: Sreedhar Jyothigowdanapura Vyasarao, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 275 days.

(21) Appl. No.: 13/625,890

(22) Filed: Sep. 25, 2012

(65) Prior Publication Data

US 2013/0085320 A1    Apr. 4, 2013

(30) Foreign Application Priority Data

Sep. 29, 2011 (IN) ............................ 3388/CHE/2011

(51) Int. Cl.
*A61G 11/00* (2006.01)
*A61M 16/16* (2006.01)

(52) U.S. Cl.
CPC ............. *A61G 11/002* (2013.01); *A61M 16/16* (2013.01); *A61G 11/003* (2013.01); *A61G 11/005* (2013.01); *A61G 11/008* (2013.01); *A61G 2203/46* (2013.01)

(58) Field of Classification Search
CPC ............... A61G 11/00; A61G 11/001–11/009; A61M 16/16; A61M 16/161; F24F 6/14; F24F 2006/143; F24F 2006/146
USPC ...................................................... 600/21–22
See application file for complete search history.

(56) References Cited

U.S. PATENT DOCUMENTS

| 3,858,570 | A | * | 1/1975 | Beld et al. ........................ 600/22 |
| 5,653,227 | A | * | 8/1997 | Barnes et al. ............ 128/203.12 |
| 5,759,149 | A | * | 6/1998 | Goldberg et al. ............... 600/22 |
| 2011/0130620 | A1 | * | 6/2011 | Dmello et al. .................. 600/22 |

OTHER PUBLICATIONS

Sung Mi Kim, et al. "Improved Care and Growth Outcomes by Using Hybrid Humidified Incubators in Very Preterm Infants." Official Journal of the American Academy of Pediatrics 2010. Originally published online Dec. 21, 2009. DOI: 10.152/peds. 2008-2997.

* cited by examiner

Primary Examiner — Charles A Marmor, II
Assistant Examiner — Carrie R Dorna
(74) Attorney, Agent, or Firm — GE Global Patent Operation; Marc A. Vivenzio

(57) ABSTRACT

An incubator to maintain environmental conditions suitable for an infant is provided. The incubator comprises a vertical support structure with a plurality of horizontal columns connected to a bottom end of the vertical support structure to form a base portion. A crib is mounted on to the vertical support structure above the base portion for supporting the infant. The crib comprises a base plate and a plurality of plates arranged in a predetermined manner to form side walls of the crib. At least one dispenser nozzle is provided in the side walls for supplying water vapors to the crib. A humidification system, attachable at least to the base portion of the incubator, is fluidly connected to the inlets of the dispenser nozzles for supplying the water vapors. A radiant warmer is mounted on a top end of the vertical support structure for supplying radiant heat energy to the crib.

14 Claims, 5 Drawing Sheets

INCUBATOR AND METHOD THEREOF

BACKGROUND OF THE INVENTION

Embodiments of the invention relate to an incubator. More particularly, the subject matter relates to a crib of the incubator.

An incubator is an apparatus used to maintain environmental conditions suitable for an infant. It is used in preterm births or for some ill full-term babies to maintain environmental conditions.

The use of incubators for maintaining the environmental conditions suitable for an infant is known in the art. The conventional incubators comprise a bassinet enclosed by a hood/canopy in which an infant can be kept in a controlled environment for medical care.

The conventional incubators comprise a heater and a fan to circulate the warmed air to the enclosure through convection. Said heater is interfaced with the control unit for maintaining the uniform temperature inside the bassinet. The incubator further comprises a humidifier for maintaining humidity inside the bassinet. A plurality of access ports are provided in the bassinet for nursing care.

In conventional incubators, it is difficult to access the infant placed in the incubators basinet. This is because the basinet is enclosed by a hood/canopy. The hood/canopy is used to enclose the basinet to maintain humidity in the basinet. This type of design results in an increase in the number of components in the incubator, and in turn increases the cost of the incubator. Further the hood/canopy occupies a large amount of space around the incubator.

Hence there exists a need to provide a simple and efficient humidifying mechanism in an infant warmer, without dependent on a hood/canopy. Further, the infant should be easily accessible for the mother and the caregiver.

BRIEF DESCRIPTION OF THE INVENTION

According to an embodiment of the present invention, a crib of an incubator is provided. The crib comprises: a base plate; a plurality of plates arranged to form side walls of the crib; and at least one dispenser nozzle disposed in at least one of the plurality of plates, the at least one dispenser nozzle being configured to supply water vapors to create a virtual vapor envelope inside the crib.

According to another embodiment of the present invention, an incubator is provided. The incubator comprises: a vertical support structure; a plurality of horizontal columns connected to a bottom end of the vertical support structure to form a base portion of the incubator; a humidification system attachable to at least the base portion; a radiant warmer mounted on a top end of the vertical support structure; and a crib detachably mounted on the vertical support structure above the base portion, the crib comprising: a base plate; a plurality of plates arranged to form side walls of the crib; and at least one dispenser nozzle disposed in at least one of the plurality of plates the at least one dispenser nozzle being configured to supply water vapors to create a virtual vapor envelope inside the crib, wherein the radiant heat warmer is configured to supply a radiant heat energy to the crib of the incubator, and wherein the at least one dispenser nozzle comprises an inlet fluidly connected to the humidification system.

According to another embodiment of the present invention, a method to control humidity in a crib of an incubator is provided. The method comprises: measuring humidity inside the crib using at least one humidification sensor; comparing the measured humidity value with a preset humidity value using a control unit; and controlling a supply of water vapors through a dispenser nozzle disposed on a side wall of the crib based on a comparison by the control unit, wherein the control unit regulates at least one of a humidification system and a solenoid valve to control the supply of the water vapors.

The foregoing summary is illustrative only and is not intended to be in any way limiting. In addition to the illustrative aspects and features described above, further aspects, and features will become apparent by reference to the drawings and the following detailed description.

BRIEF DESCRIPTION OF THE DRAWINGS

The novel features and characteristics of the disclosure are set forth in the appended claims. The disclosure itself, however, as well as a preferred mode of use, further objectives and advantages thereof, will best be understood by reference to the following detailed description of an illustrative aspect when read in conjunction with the accompanying figures. One or more aspects are now described, by way of example only, with reference to the accompanying figures wherein like reference numerals represent like elements and in which:

The figures depict aspects of the disclosure for purposes of illustration only. One skilled in the art will readily recognize from the following description that alternative aspects of the structures and methods illustrated herein may be employed without departing from the principles of the disclosure described herein.

DETAILED DESCRIPTION OF THE INVENTION

The foregoing has broadly outlined the features and technical advantages of the present disclosure in order that the detailed description of the disclosure that follows may be better understood. Additional features and advantages of the disclosure will be described hereinafter which foam the subject of the claims of the disclosure. It should be appreciated by those skilled in the art that the conception and specific aspect disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

Figure 1:
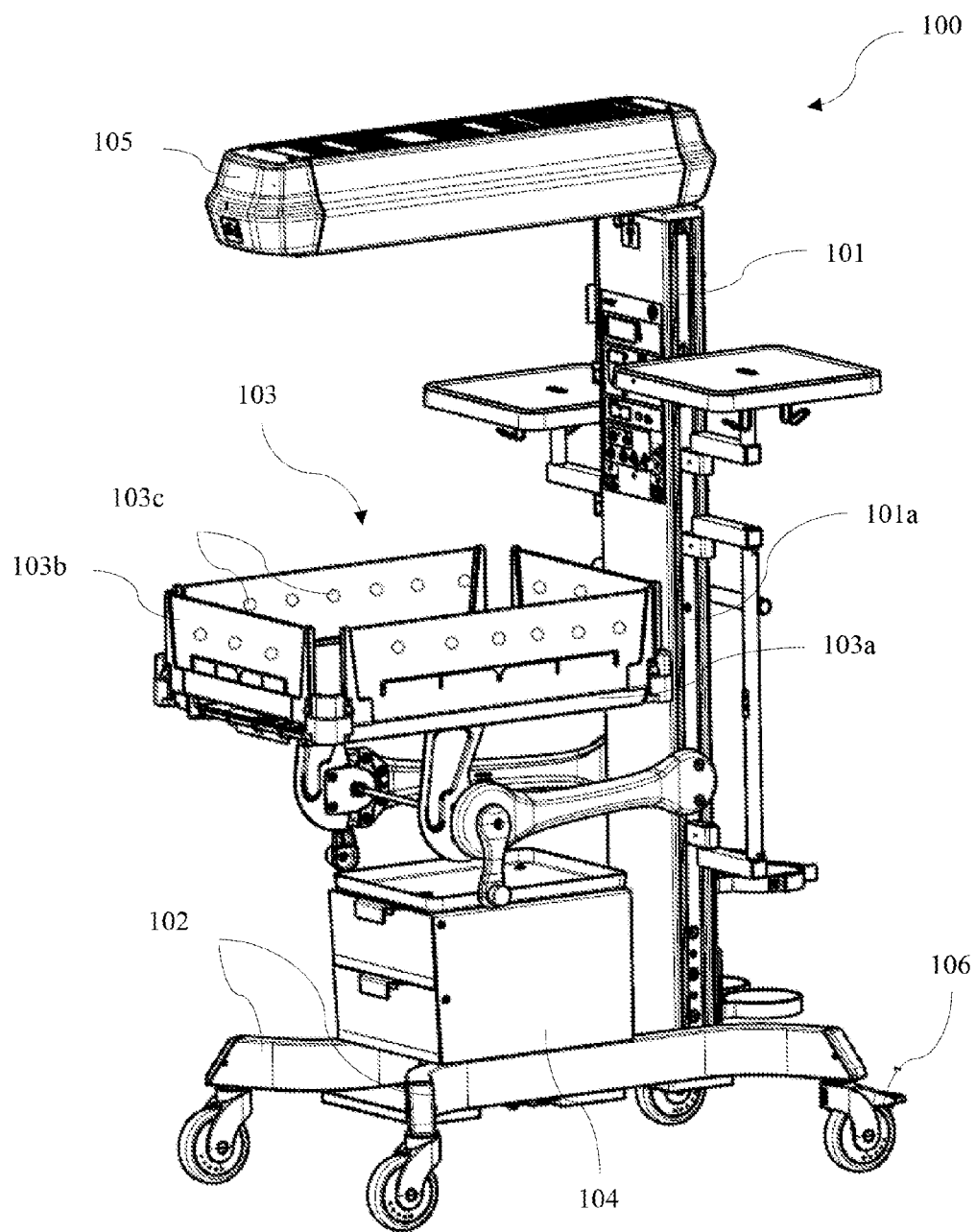
FIG. 1 illustrates a perspective view of the incubator according to an embodiment of the present invention.

FIG. 1 is an exemplary embodiment of the invention illustrating a perspective view of an incubator (100). The incubator (100) comprises a vertical support structure (101) for supporting components of the incubator (100). A plurality of horizontal columns (102) connected to a bottom of the vertical support structure (101) form a base portion of the incubator (100). A crib (103) of predetermined shape is mounted on the vertical support structure (101) above the base portion (102) in which an infant can be kept in a controlled environment for medical care. The crib (103) comprises a base plate (103a) for supporting the infant and a plurality of plates arranged in a predetermined pattern around the base plate (103a) to form side walls (103b) of the crib (103). In one aspect, the side walls (103b) can be hollow columns which are made of multi plates and solid plates or their combinations. A plurality of dispenser nozzles (103c) are provided in the side walls (103b) of the crib (103) for supplying water vapors to the crib (103).

Figure 2:
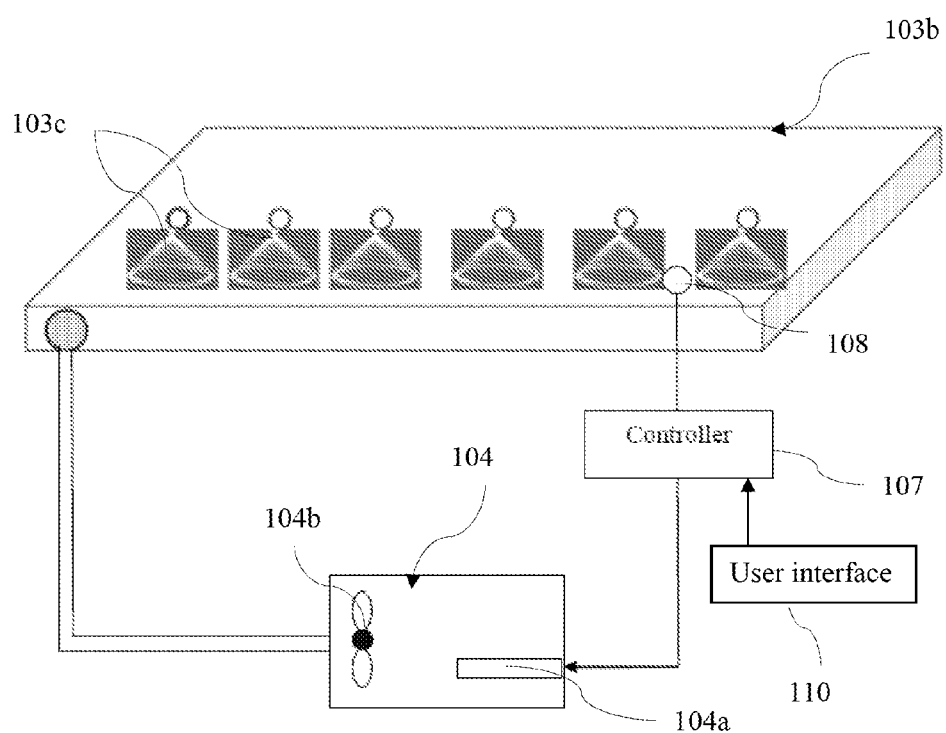
FIG. 2 illustrates a schematic view of system to control the humidification in the crib according to an embodiment of the present invention.

A humidification system (104) is attachable to base portion (102) of the incubator (100) and said humidification system (104) is fluidly connected to inlets of the dispenser nozzles (103c) for supplying the water vapors to the crib (103). Alternately, the humidifying system could be attachable to the crib (103), particularly to the base portion of the crib (103a). As shown in FIG. 2, the humidification system (104) comprises a humidification unit (104a) for converting the water into water vapor and a blower fan (104b) for increasing the draft of the water vapor to supply the same to the dispenser nozzles (103c).

According to an embodiment of the present invention, the humidification system (104) is selected from a group comprising, but not limited to, evaporative humidifiers, piezo electric ultrasonic humidifiers, impeller humidifiers and steam humidifiers.

According to another embodiment of the present invention, the humidification unit (104a) is a piezo electric ultrasonic humidification unit which converts water into a cool mist. The piezo electric ultrasonic humidification unit comprises a metal diaphragm vibrating at an ultrasonic frequency to create water droplets which exit the humidifier in the form of a cool fog. Ultrasonic humidifiers use a piezo electric transducer to create a high frequency mechanical oscillation in a body of water. The water tries to follow the high frequency oscillation but cannot because of its comparative weight and mass inertia. Thus, a momentary vacuum is created on the negative oscillation, causing the water to cavitate into vapor.

According to another embodiment of the present invention, the humidification unit (104a) is a steam humidifier which converts the water into water vapor. The steam humidifiers are also called vaporizers, which boil the water, releasing steam and moisture into the air.

A radiant warmer (105) is mounted on a top end of the vertical support structure (101) and horizontally above the crib (103). Said radiant warmer (105) supplies heat to said crib (103) for maintaining environmental conditions suitable for an infant inside the crib (103). The radiant warmer (105) comprises a tubular heater which is heated by infrared radiation, and supply the heat to the crib (103). The radiant warmer (105) output is controlled by a servo controller which takes input from a temperature sensor placed on the infant. The temperature sensor measures the body temperature of the infant, and gives signal to the servo controller. The servo controller compares the measured value of temperature with the preset value and accordingly controls the output of the radiant warmer (105). The radiant warmer (105) works through the water vapor and creates required warmth to the infant.

According to another embodiment of the present invention, the vertical support structure (101) comprises a plurality of guide rails (101a) on its side walls for facilitating the vertical movement of radiant warmer (105) and the crib (103). The crib (103) can be moved vertically to support the infant at any desired position and the radiant warmer (105) can be moved vertically to supply heat to the crib (103).

According to another embodiment of the present invention, a plurality of wheels (106) is provided at the bottom ends of the base portion (102) for facilitating maneuverability of the incubator (100).

FIG. 2 is an exemplary embodiment which illustrates a schematic view of a system to control humidity in the crib. The figure shows one side wall (103b) of the crib (103) with a plurality of dispenser nozzles (103c) in it. A plurality of humidification sensors (108) are mounted in predetermined locations of the crib (103) for measuring the relative humidity in the crib (103). The humidification sensors (108) are interfaced with a control unit (107) for controlling the relative humidity inside the crib (103).

According to another embodiment of the present invention, the control unit (107) is interfaced with the piezo electric transducer of the humidification system (104) for regulating the flow of water vapors through the dispenser nozzles (103c). The control unit (107) compares the measured value of humidity with the preset value of humidity and accordingly varies the amplitude of vibration of the piezo electric transducer to regulate the conversion rate of water into water vapors. A blower fan (104b) is used to blow the water vapors to the dispenser nozzles (103c) through a water vapor flow channel.

Figure 3:
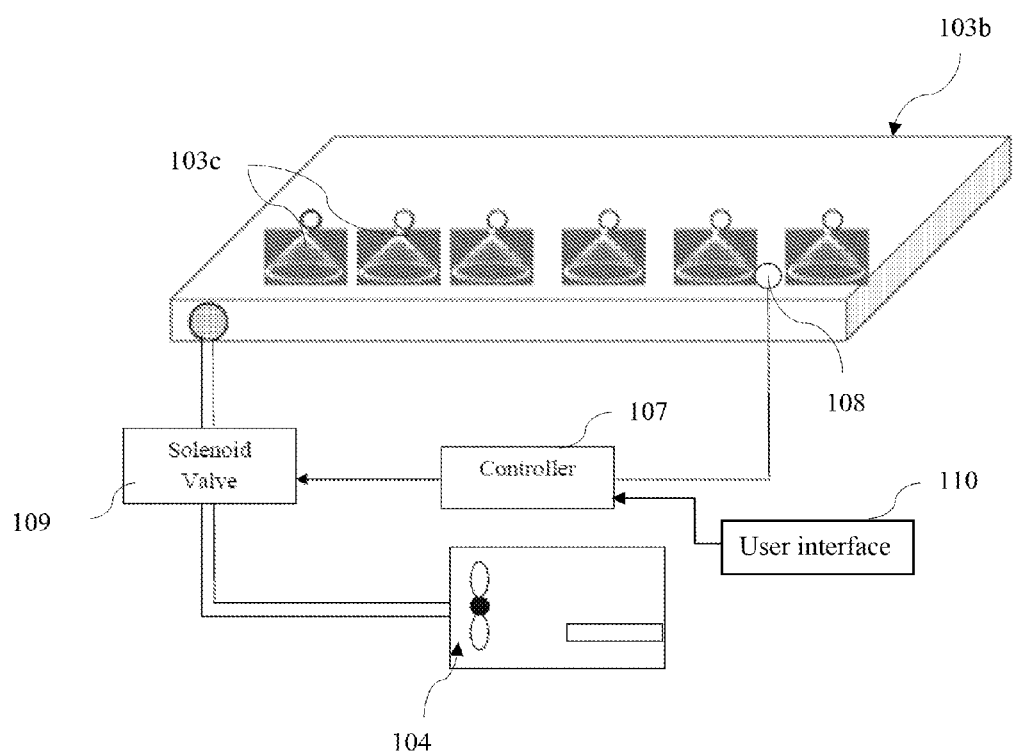
FIG. 3 illustrates a schematic view of a system to control the humidification in the crib using solenoid valve according to an embodiment of the present invention.

According to another embodiment of the present invention, the control unit (107) is interfaced with a solenoid valve (109) provided in the water vapor flow line regulating the flow of water vapors through the dispenser nozzles (103c) as shown in FIG. 3. The control unit (107) compares the measured value of humidity with a preset value of humidity and accordingly varies the flow rate of water vapors passing through the dispenser nozzles (103c) by regulating the solenoid valve (109). In one embodiment of the disclosure, a solenoid valve (109) or similar flow controlling mechanism can be connected to each of the dispenser nozzles (103c) for controlling the supply of water vapors through each dispenser nozzle (103c). This facilitates controlled humidity in various parts of the crib (103). Further the user can set predefined humidity level for different parts of the crib through the user interface (110)

A user interface (110) is provided in the incubator (100) for inputting the values of humidity and the temperature by the user based on the requirement. The user interface (110) is interfaced with the control unit (107) for presetting the humidity value based on comfort level of an infant. The control unit (107) maintains the preset value of humidity inside the crib (103) by regulating the humidification system and/or solenoid valve (110) to control the rate of flow of water vapors through the dispenser nozzles (103c).

According to another embodiment of the present invention, the plates of the side walls (103b) are hollow plates of rectangular cross section. The dispenser nozzles (103c) are placed in the hollow portion of the plates having an outlet towards inside chamber of the crib (103).

Figure 4:
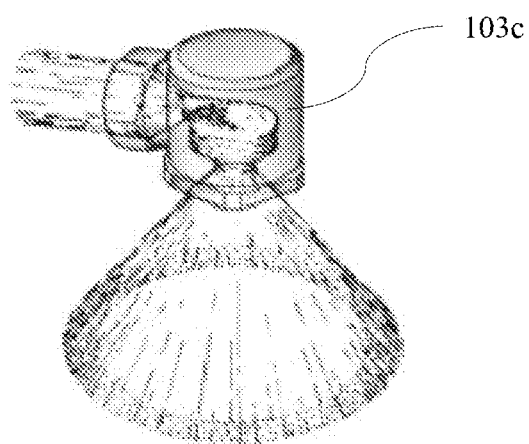
FIGS. 4 and 5 illustrate perspective views of dispenser nozzles according to an embodiment of the present invention.
Figure 5:
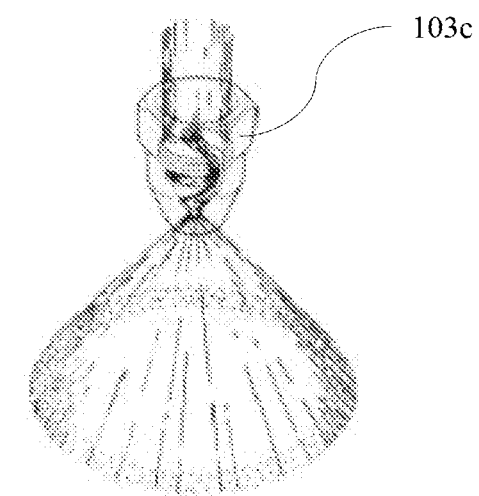

FIGS. 4 and 5 are exemplary embodiments illustrating a perspective view of dispenser nozzles (103c). The dispenser nozzles (103c) are arranged in the side walls (103b) of the crib (103) to supply the water vapors for creating the virtual vapor envelope inside the crib (103). The inlets of the dispenser nozzles (103c) are fluidly connected to the humidification system (104) for receiving the water vapors. The dispenser nozzles (103c) are selected from a group comprising, but not limited to, hollow cone nozzles, full cone nozzles and Disc-Core type cone spray nozzles or any other nozzles which serve the purpose. The dispenser nozzles (103c) spray the water vapors in a circular manner and create a virtual vapor envelope above the mattress encompassing the infant under care.

According to another embodiment of the present invention, the spray pattern of the hollow cone nozzle is a circular ring and said pattern is achieved by the use of an inlet orifice tangential to a cylindrical swirl chamber that is open at one end. The circular orifice exit has a diameter smaller than the swirl chamber. The whirling liquid results in a circular shape; the center of the ring is hollow. Hollow cone nozzles are used for applications requiring good atomization of liquids at low pressures or when quick heat transfer is needed. These nozzles also feature large and unobstructed flow passages, which provide a relatively high resistance to clogging. Hollow cone nozzles provide the smallest drop size distributions.

According to another embodiment of the present invention, the fill cone nozzles yield complete spray coverage in a round, oval or square shaped area. Usually the liquid is swirled within the nozzle and mixed with non-spinning liquid that has bypassed an internal vane. Liquid then exits through an orifice, forming a conical pattern. Spray angle and liquid distribution within the cone pattern depend on the vane design and location relative to the exit orifice. The exit orifice design and the relative geometric proportions also affect the spray angle and distribution. Full cone nozzles provide a uniform spray distribution of medium to large size drops resulting from their core design, which features large flow passages.

Figure 6:
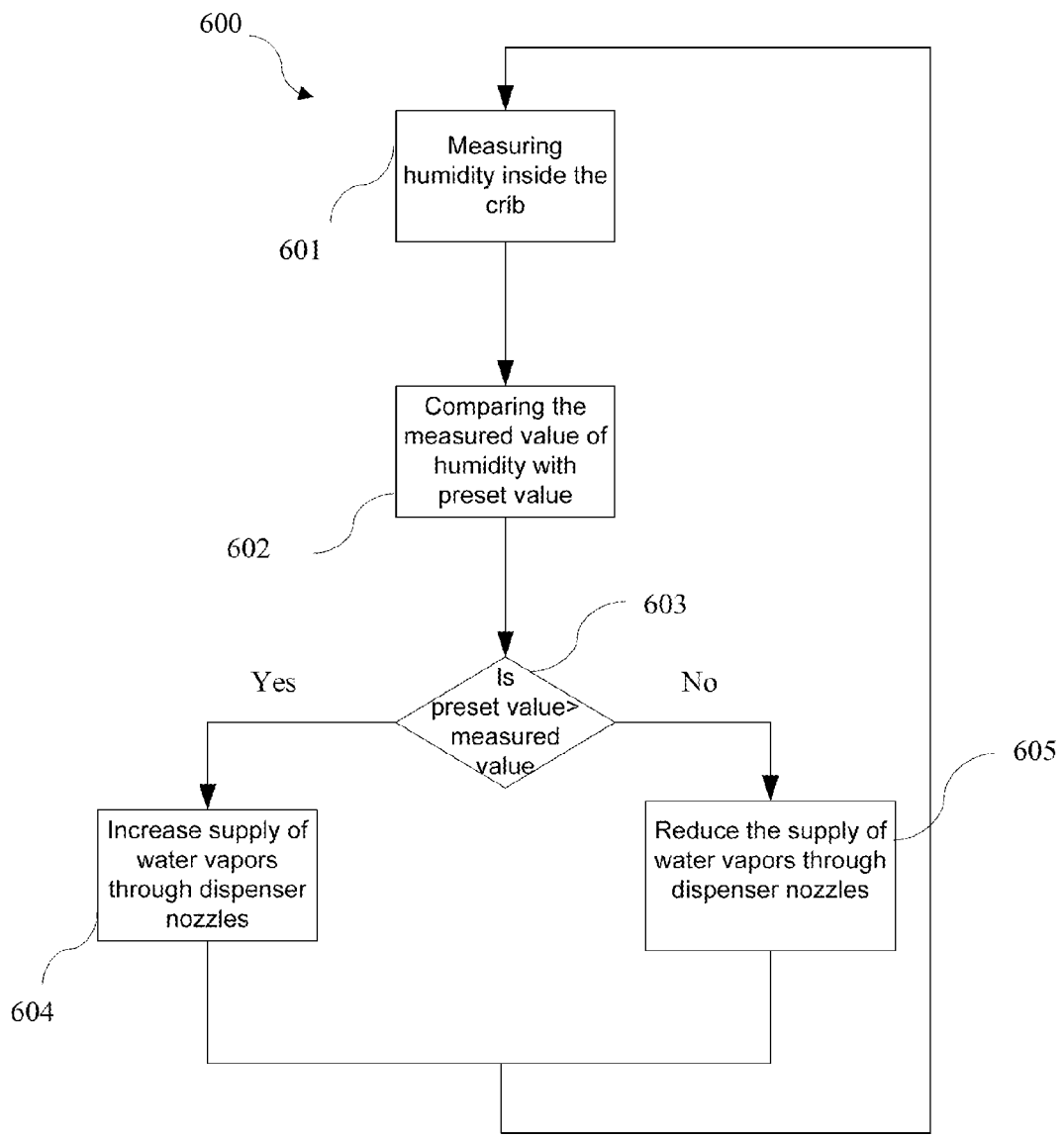
FIG. 6 illustrates a flow chart of a method of controlling humidity inside the crib of the incubator according to an embodiment of the present invention.

FIG. 6 is an exemplary embodiment which illustrates a flow chart of a method of controlling humidity inside the crib (103) of the incubator (100). The humidification sensor (108) measures the humidity inside the crib (103) and provides a signal to the control unit (107) as shown in (601). The control unit (107) compares the measured value of humidity with a preset value of humidity as shown in (602). If the preset value of humidity is less than the measured value as shown in (603), then the supply of water vapors through the dispenser nozzles (103c) is increased as shown in (604). For any other measured value of the humidity, the supply of water vapors through the dispenser nozzles (103c) is reduced as shown in (605).

According to another embodiment of the present invention, the control unit (107) regulates either of a humidification system (104) or a solenoid valve (109) to control the supply of water vapors through the dispenser nozzles (103c). In one embodiment, both humidification system (104) and solenoid valve (109) can be regulated to control the supply of water vapors through the dispenser nozzles (103c).

Thus embodiments of the present invention provide an incubator and a method for controlling the humidity in an incubator. The incubator facilitates elimination of a hood/canopy for providing humidity within the crib and controls humidity without considerable water loss due to open environment. Further, infant access is made easy for the mother and the caregiver due to the structure of the incubator.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A crib of an incubator, the crib comprising:
a base plate;
a plurality of plates arranged to form side walls of the crib; and
a plurality of dispenser nozzles disposed in at least one of the plurality of plates, wherein each of the plurality of dispenser nozzles is fluidly connected to a flow controlling mechanism that selectively controls the supply of water vapors through each of the plurality of dispenser nozzles individually, and the plurality of dispenser nozzles are configured to create a virtual vapor envelope inside the crib.

2. The crib according to claim 1, wherein each dispenser nozzle is selected from a hollow cone nozzle, a full cone nozzle, a Disc-Core type cone spray nozzle, and combinations thereof.

3. The crib according to claim 1, wherein each dispenser nozzle comprises an inlet, the inlet being fluidly connected to a humidification system.

4. The crib according to claim 1 comprising at least one of the dispenser nozzles disposed in each of the plurality of plates, wherein each of the dispenser nozzles is configured to supply the water vapors to create the virtual vapor envelope inside the crib.

5. The crib according to claim 1, further comprising a humidification system attachable to the base plate.

6. An incubator comprising:
a vertical support structure;
a plurality of horizontal columns connected to a bottom end of the vertical support structure to form a base portion of the incubator;
a humidification system attachable to at least the base portion;
a radiant warmer mounted on a top end of the vertical support structure; and
a crib detachably mounted on the vertical support structure above the base portion, the crib comprising:
a base plate;
a plurality of plates arranged to form side walls of the crib; and
a plurality of dispenser nozzles disposed in at least one of the plurality of plates, the plurality of dispenser nozzles being configured to supply water vapors to create a virtual vapor envelope inside the crib,
wherein the radiant heat warmer is configured to supply a radiant heat energy to the crib of the incubator, and wherein each of the plurality of dispenser nozzles comprise an inlet fluidly connected to a flow controlling mechanism that selectively controls the supply water vapors through each of the plurality of dispenser nozzles individually from the humidification system.

7. The incubator according to claim 6, wherein the vertical support structure comprises a plurality of guide rails disposed on the side walls to facilitate vertical movement of the radiant warmer and the crib.

8. The incubator according to claim 6, wherein the humidification system comprises at least one humidification sensor to measure the humidity inside the crib.

9. The incubator according to claim 8 further comprising a control unit, wherein the humidification sensor is configured to provide a signal to the control unit.

10. The incubator according to claim 8 further comprising a control unit, wherein the control unit is connected to at least one of the humidification system and at least one solenoid valve, and wherein the control unit is configured to control the water vapors supplied to the plurality of dispenser nozzles.

11. A method to control humidity in a crib of an incubator, the method comprising:
   measuring humidity inside the crib using a plurality of humidification sensors;
   comparing the measured humidity from each of the humidification sensors with preset humidity values using a control unit; and
   controlling a supply of water vapors through a plurality of dispenser nozzles disposed on side walls of the crib based on a comparison by the control unit, wherein the control unit regulates at least one of a humidification system and solenoid valves to control the supply of the water vapors to each of the plurality of dispenser nozzles individually.

12. The method according to claim 11, further comprising providing the preset humidity values to the control unit through a user interface.

13. The method according to claim 11, further comprising reducing the supply of the water vapors through at least one of the dispenser nozzles if the measured humidity is greater than at least one of the preset humidity values.

14. The method according to claim 11, further comprising increasing the supply of the water vapors through at least one of the dispenser nozzles if the measured humidity is less than at least one of the preset humidity values.

* * * * *

UNITED STATES PATENT AND TRADEMARK OFFICE
CERTIFICATE OF CORRECTION

PATENT NO. : 9,168,194 B2  
APPLICATION NO. : 13/625890  
DATED : October 27, 2015  
INVENTOR(S) : Vyasarao Page 1 of 1

It is certified that error appears in the above-identified patent and that said Letters Patent is hereby corrected as shown below:

In the specification

In Column 2, Line 51, delete "foam" and insert -- form --, therefor.

In Column 3, Line 24, delete "crib (103a)." and insert -- crib (103). --, therefor.

In Column 4, Line 55, delete "valve (110)" and insert -- valve (109) --, therefor.

In Column 5, Line 22, delete "the fill" and insert -- the full --, therefor.

In the claims

In Column 6, Line 49, in Claim 6, delete "radiant heat" and insert -- radiant --, therefor.

In Column 6, Line 53, in Claim 6, delete "supply" and insert -- supply of --, therefor.

Signed and Sealed this  
Fifth Day of July, 2016

Michelle K. Lee  
*Director of the United States Patent and Trademark Office*